(12) United States Patent
Peterson et al.

(10) Patent No.: US 9,289,149 B2
(45) Date of Patent: Mar. 22, 2016

(54) APPARATUS AND METHOD FOR WIRELESSLY TRANSFERRING AND STORING MEDICAL DATA

(75) Inventors: James R. Peterson, Fond du Lac, WI (US); Sarah Alme, Milwaukee, WI (US)

(73) Assignee: General Electric Company, Schenectady, NY (US)

( * ) Notice: Subject to any disclaimer, the term of this patent is extended or adjusted under 35 U.S.C. 154(b) by 2005 days.

(21) Appl. No.: 11/746,971

(22) Filed: May 10, 2007

(65) Prior Publication Data

US 2008/0281217 A1    Nov. 13, 2008

(51) Int. Cl.
*A61B 5/00* (2006.01)
*A61B 5/0432* (2006.01)
*A61N 1/372* (2006.01)

(52) U.S. Cl.
CPC ........... *A61B 5/04325* (2013.01); *A61B 5/0006* (2013.01); *A61N 1/37223* (2013.01); *A61B 2560/0412* (2013.01)

(58) Field of Classification Search
CPC ............... A61B 5/0006; A61B 5/0002; A61B 5/04325; A61N 1/37252; A61N 1/37223
USPC ............................ 600/508, 523, 544; 607/32
See application file for complete search history.

(56) References Cited

U.S. PATENT DOCUMENTS

| 5,111,396 | A | | 5/1992 | Mills et al. |
|---|---|---|---|---|
| 6,141,588 | A | * | 10/2000 | Cox et al. ........................ 607/9 |
| 6,577,893 | B1 | * | 6/2003 | Besson et al. ................ 600/509 |
| 2005/0206518 | A1 | * | 9/2005 | Welch et al. ............. 340/539.12 |

\* cited by examiner

*Primary Examiner* — Tammie K Heller
(74) *Attorney, Agent, or Firm* — Andrus Intellectual Property Law, LLP

(57) ABSTRACT

A medical diagnostic/monitoring system is disclosed herein. The medical diagnostic/monitoring system includes a data acquisition device having a first near field communication device, and a data storage device wirelessly connected to the data acquisition device. The data storage device includes a second near field communication device. The first near field communication device and the second near field communication device are collectively configured to wirelessly transfer power and data from the data acquisition device to the data storage device.

7 Claims, 1 Drawing Sheet

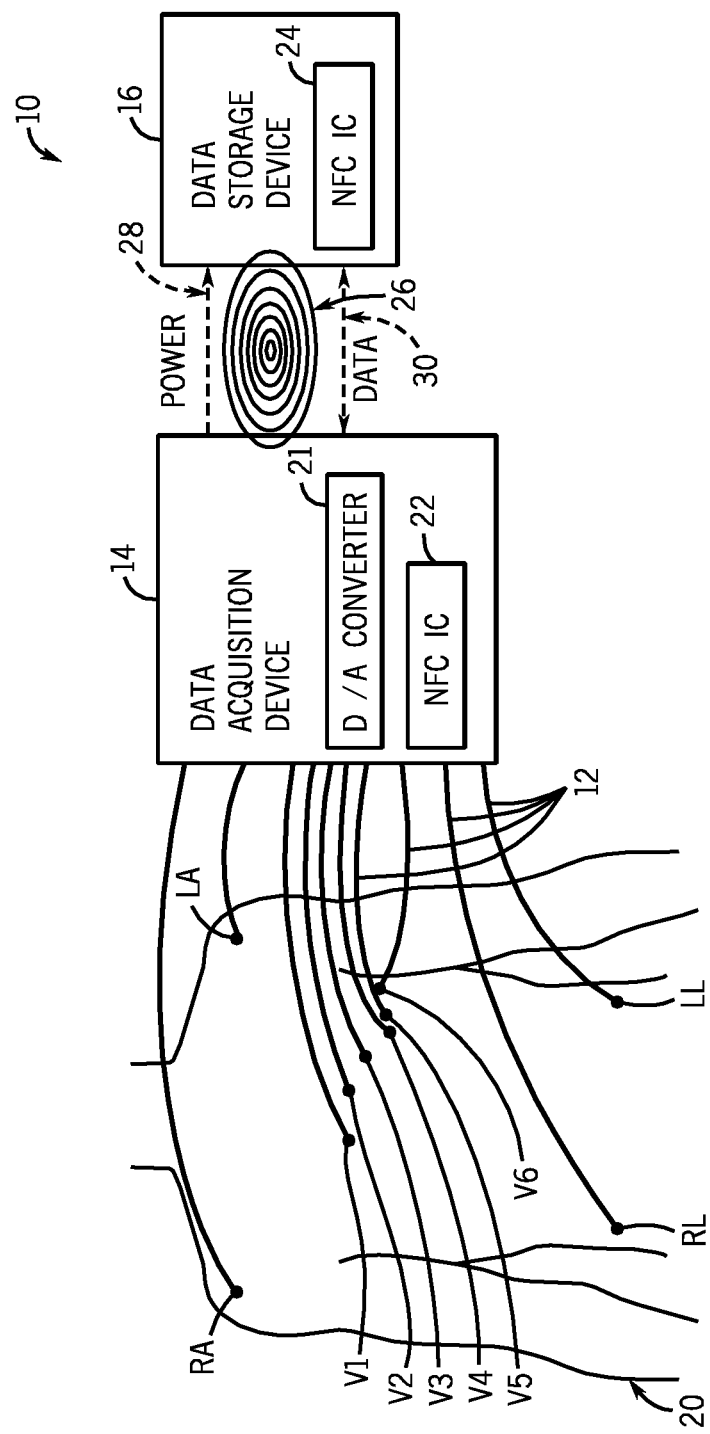

APPARATUS AND METHOD FOR WIRELESSLY TRANSFERRING AND STORING MEDICAL DATA

FIELD OF THE INVENTION

This disclosure relates generally to an apparatus and method for wirelessly transferring and storing medical data.

BACKGROUND OF THE INVENTION

Performing medical diagnostic measurements if the field commonly requires the transfer and/or storage of the acquired measurement data to a centralized site. For example, after performing an electrocardiogram (ECG) in the field, the ECG data is generally transferred to the central computer of a hospital for further analysis. It is known to transfer acquired measurement data using telephone modems or an Internet connection. One problem is that there are situations in which telephone or Internet connections are not available or are not economically feasible.

It is also known to transfer measurement data acquired in the field using portable media interfaces such as USB drives or flash memory cards. One problem with portable media interfaces is that they require the implementation of an electrical connector to physically couple the portable media interface with the data acquisition device. This electrical connector is often expensive. The electrical connector is also difficult to clean as it generally includes recessed portions that are hard to access with cleaning instruments. The inherent difficulty with cleaning conventional electrical connectors adds to the expense of performing a given medical procedure and also increases the risks associated with bacterial and viral contamination. Another problem with portable media interfaces is that they are difficult to externally label thereby increasing the likelihood that the data will be inaccurately processed and/or that the data will be correlated with the wrong patient.

BRIEF DESCRIPTION OF THE INVENTION

The above-mentioned shortcomings, disadvantages and problems are addressed herein which will be understood by reading and understanding the following specification.

In an embodiment, a medical diagnostic/monitoring system includes a data acquisition device having a first near field communication device, and a data storage device wirelessly connected to the data acquisition device. The data storage device includes a second near field communication device. The first near field communication device and the second near field communication device are collectively configured to wirelessly transfer power and data from the data acquisition device to the data storage device.

In another embodiment, an electrocardiogram system includes a sensor, a conductor connected to the sensor, and a data acquisition device connected to the conductor. The data acquisition device includes a first near field communication device. The electrocardiogram system also includes a radio frequency identification memory card wirelessly connected to the data acquisition device. The radio frequency identification memory card includes a second near field communication device. The first near field communication device and the second near field communication device are collectively configured to wirelessly transfer power and data from the data acquisition device to the radio frequency identification memory card.

In another embodiment, a method for wirelessly transferring electrocardiogram data to a data storage device includes generating an electromagnetic field using a near field communication device, implementing the electromagnetic field to wirelessly transfer power from a data acquisition device to a radio frequency identification memory card, and implementing the electromagnetic field to wirelessly transfer electrocardiogram data from the data acquisition device to the radio frequency identification memory card.

Various other features, objects, and advantages of the invention will be made apparent to those skilled in the art from the accompanying drawings and detailed description thereof.

BRIEF DESCRIPTION OF THE DRAWINGS

FIG. 1 is a schematic diagram illustrating a patient connected to a medical diagnostic/monitoring system in accordance with an embodiment.

DETAILED DESCRIPTION OF THE INVENTION

In the following detailed description, reference is made to the accompanying drawings that form a part hereof, and in which is shown by way of illustration specific embodiments that may be practiced. These embodiments are described in sufficient detail to enable those skilled in the art to practice the embodiments, and it is to be understood that other embodiments may be utilized and that logical, mechanical, electrical and other changes may be made without departing from the scope of the embodiments. The following detailed description is, therefore, not to be taken as limiting the scope of the invention.

Referring to FIG. 1, a schematically represented medical diagnostic/monitoring system 10 is shown. The medical diagnostic/monitoring system 10 will hereinafter be described as an electrocardiogram (ECG) system 10 adapted measure the electrical signals generated by a patient's heart. It should, however, be appreciated that the medical diagnostic/monitoring system 10 may also include other systems and devices such as, for example, an electroencephalogram (EEG) system, a blood pressure monitor, a pulse oximeter, a thermometer, etc.

The ECG system 10 includes a plurality of sensors or transducers such as the electrodes RA, LA, V1, V2, V3, V4, V5, V6, RL and LL, a plurality of conductors such as the lead wires 12, a data acquisition device 14, and a data storage device 16.

In the embodiment depicted in FIG. 1, the electrode RA is applied to the patient's right arm; the electrode LA is applied to the patient's left arm; the electrodes V1, V2, V3, V4, V5 and V6 are applied to the patient's chest; the electrode RL is applied to the patient's right leg; and the electrode LL is applied to the patient's left leg. This application of the electrodes provides a standard twelve lead, ten-electrode ECG signal. It should be appreciated that the electrode configuration of FIG. 1 is provided for illustrative purposes, and that other electrode configurations can be envisioned. The electrodes RA, LA, V1, V2, V3, V4, V5, V6, RL and LL are adapted to sense or detect cardiac electrical signals generated by the patient's heart, and to generate analog signals proportional to the detected cardiac electrical signals.

The lead wires 12 each couple one of the electrodes RA, LA, V1, V2, V3, V4, V5, V6, RL and LL with the data acquisition device 14. The lead wires 12 are configured to transmit the analog signals from the electrodes RA, LA, V1, V2, V3, V4, V5, V6, RL and LL to the data acquisition device 14.

The data acquisition device 14 may optionally include a digital/analog (D/A) converter 21. The D/A converter 21 is configured to convert the analog signals from the electrodes RA, LA, V1, V2, V3, V4, V5, V6, RL and LL into digital signals.

The data acquisition device 14 is adapted to wirelessly transfer data obtained from the electrodes RA, LA, V1, V2, V3, V4, V5, V6, RL and LL, to the data storage device 16. The data acquisition device 14 implements a near field communication (NFC) integrated circuit (IC) 22 configured to facilitate the wireless transfer of data as will be described in detail hereinafter. Advantageously, the implementation of the NFC IC 22 reduces the cost of the data acquisition device 14. More precisely, the NFC IC 22 obviates the need for one or more conventional electrical connectors as components of the data acquisition device 14. As the NFC IC 22 is generally less expensive than conventional electrical connectors, replacing one or more electrical connectors with the NFC IC 22 reduces the overall cost of the data acquisition device 14.

The data acquisition device 14 is also easier to clean and sterilize because of the incorporation of the NFC IC 22. More precisely, the NFC IC 22 obviates the need for one or more conventional electrical connectors having exposed recessed portions that are difficult to access with a cleaning instrument. In contrast, the NFC IC 22 can be disposed entirely within the data acquisition device 14 such that the NFC IC 22 does not interfere with the process of cleaning or sterilizing the outer surface of the data acquisition device 14. Simplifying the process of cleaning and sterilizing the data acquisition device 14 reduces the labor and cost for a given medical procedure and also reduces the risks associated with bacterial and viral contamination.

The NFC IC 22 of the data acquisition device 14 works in combination with a NFC IC 24 of the data storage device 16 in the following manner. The NFC IC 22 and the NFC IC 24 function together to produce an electromagnetic field 26 that is operable to wirelessly transmit power 28 from the data acquisition device 14 to the data storage device 16, and to wirelessly transmit data 30 back and forth between the data acquisition device 14 and the data storage device 16. Near field communication is well known to those skilled in the art and therefore will not be described in detail.

The transmission of power 28 from the data acquisition device 14 to the data storage device 16 allows the data storage device 16 to operate without its own dedicated power supply. The elimination of a dedicated power supply allows for a lighter and less expensive data storage device 16.

The wireless transmission of data 34 from the data acquisition device 14 to the data storage device 16 obviates the need for a conventional electrical connector as a component of the data storage device 16. Accordingly, the requisite cost and weight of the data storage device 16 are reduced.

The wireless transmission of data 34 from the data storage device 16 to the data acquisition device 14 may be useful, for example, so that the data storage device 16 can provide data transmission instructions. According to one embodiment, the data storage device 16 could wirelessly send the data acquisition device 14 instructions dictating the specific type of data to be transmitted. According to another embodiment, the data storage device 16 could wirelessly send the data acquisition device 14 instructions dictating the manner in which data is to be transmitted.

The data storage device 16 may include a radio frequency identification (RFID) memory card also commonly referred to as a proximity integrated circuit card (PICC). Advantageously, RFID memory cards are adapted to accommodate printing (e.g., alphanumeric characters) or other graphic images. Therefore, the RFID memory cards can be customized to visually convey detailed information such as, for example, the identity of the patient, the type of collected data, the date of data collection, etc. RFID memory cards can also be compact, lightweight, and inexpensive.

While the invention has been described with reference to preferred embodiments, those skilled in the art will appreciate that certain substitutions, alterations and omissions may be made to the embodiments without departing from the spirit of the invention. Accordingly, the foregoing description is meant to be exemplary only, and should not limit the scope of the invention as set forth in the following claims.

We claim:

1. A method for wirelessly transferring physiological data to a data storage device comprising:
   obtaining physiological data with a transducer of a data acquisition device, the transducer configured to obtain the physiological data from a body of a patient;
   generating an electromagnetic field between a first near field communication device of the data acquisition device and a second near field communication device of a data storage device;
   transferring power from the data acquisition device to the data storage device across the electromagnetic field;
   transferring the physiological data from the data acquisition device to the data storage device across the electromagnetic field and
   storing the physiological data at the data storage device.

2. The method of claim 1, further comprising implementing the electromagnetic field to wirelessly transfer information from a radio frequency identification memory card of the data storage device to the data acquisition device.

3. The method of claim 1, wherein the transducer is an electrode and the physiological data is a cardiac electrical signal.

4. The method of claim 3, further comprising implementing the electrode to generate an analog signal proportional to the sensed cardiac electrical signal, and providing the analog signal from the electrode to the data acquisition device.

5. The method of claim 1, further comprising:
   storing the physiological data at a radio frequency identification memory card of the storage device.

6. The method of claim 1, wherein the data storage device comprises a radio frequency identification memory card comprising a plurality of alphanumeric characters configured to visually convey a selectable type of information.

7. The method of claim 1, wherein the data storage device comprises a radio frequency identification memory card comprising graphic image configured to visually convey information pertaining to the identity of a patient.

* * * * *